US00PP12510P2

(12) United States Plant Patent
Yokoi

(10) Patent No.: US PP12,510 P2
(45) Date of Patent: Apr. 2, 2002

(54) *EUPHORBIA CYATHOPHORA* PLANT NAMED 'YOKOI'S WHITE'

(75) Inventor: Masato Yokoi, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/311,102

(22) Filed: May 13, 1999

(51) Int. Cl.[7] ..... A01H 5/00

(52) U.S. Cl. ..... Plt./302

(58) Field of Search ..... Plt./302, 303–307

*Primary Examiner*—Bruce R. Campell
*Assistant Examiner*—June Hwu
(74) *Attorney, Agent, or Firm*—Christie, Parker & Hale, LLP

(57) ABSTRACT

A new plant variety of *Euphorbia cyathophora* named 'Yokoi's White', characterized by its distinctive cream-colored leaf variegation.

2 Drawing Sheets

BACKGROUND OF THE INVENTION

The present invention relates to a new and distinct variety of *Euphorbia cyathophora* J. Murray, which was discovered as a branch sport in a controlled planting of *Euphorbia cyathophora* in Okinawa, Japan by Dr. Masato Yokoi. The varietal denomination of the new variety is 'YOKOI'S WHITE'.

The genus Euphorbia is included in the family Euphorbiaceae which comprises about 283 genera and 7,300 species of mostly non-woody shrubs and tress, as well as a few vines, tropical and temperate in origin. Euphorbia comprises over 2,000 species of some of which possess desirable ornamental characteristics. *Euphorbia cyathophora* belongs to the small sub-genus Poinsettia Graham (1836), which comprises about 12 species of non-succulent annuals, perennials, sub-shrubs or shrubs (rarely small bush trees), of erect habit, originating in the Americas. Poinsettia is characterized by never-branching stems forming a symmetrical umbel-like structure at the top; symmetrical stem leaves at the base; glandular stipples; cyathia in congested terminal clusters, each one sub-tending a brightly colored floral leaf; reduced number of nectaries, 1 or 2 (rarely 3 or 4), lacking petaloid appendages; seeds with tubercles, and no caruncle.

*Euphorbia cyathophora* is widespread and native throughout much of tropical and sub-tropical America. It has been introduced and naturalized throughout many parts of the world, including Japan. *Euphorbia cyathophora* generally has linear to ovate or pandurate, mostly dull green in color with red blotches at the base, exhibiting a greater proportion of red as they go up the stem. *Euphorbia cyathophora* has often been misidentified, cultivated and sold under the name *Euphorbia heterophylla*. Synonyms also include *E. heterophylla* L. var. *cyathophora* (Murray) Grisebach; and *Poinsettia cyathophora* (Murray) Klotzch & Garcke ex Klotzch.

SUMMARY OF THE INVENTION

The new variety was discovered as a sport in a controlled planting of *Euphorbia cyathophora*, and differs from its parent and other varieties of *Euphorbia cyathophora* of which I am aware by its cream-colored marginal leaf variegation. Asexual reproduction of the new variety by stem cuttings performed in Okinawa Prefecture, Japan; Lewisberry, Pa.; and Fulshear, Tex. have confirmed that the distinctive characteristics of the new variety are stable and transmitted to succeeding generations, and the new variety reproduces true to type.

COMPARISON WITH PARENT

'YOKOI'S WHITE' is distinguished from its parent and all other varieties of *Euphorbia cyathophora* of which I am aware by its variegated foliage, which exhibits a 1 to 12 mm. wide cream-colored margin.

BRIEF DESCRIPTION OF ILLUSTRATIONS

The accompanying illustrations show a specimen (a single, multi-branched plant) of the new cultivar in photo illustrations as true to color as is reasonably possible to make in an illustration of this character.

Figure 1:
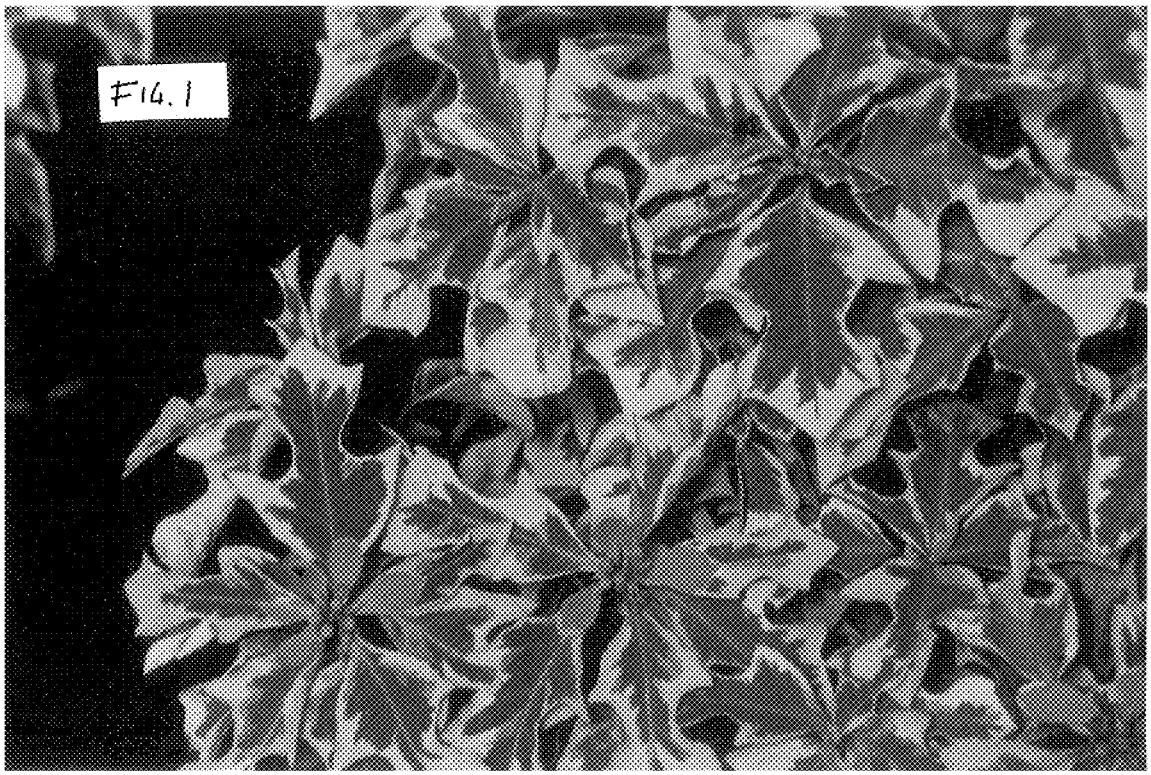
Figure 2:
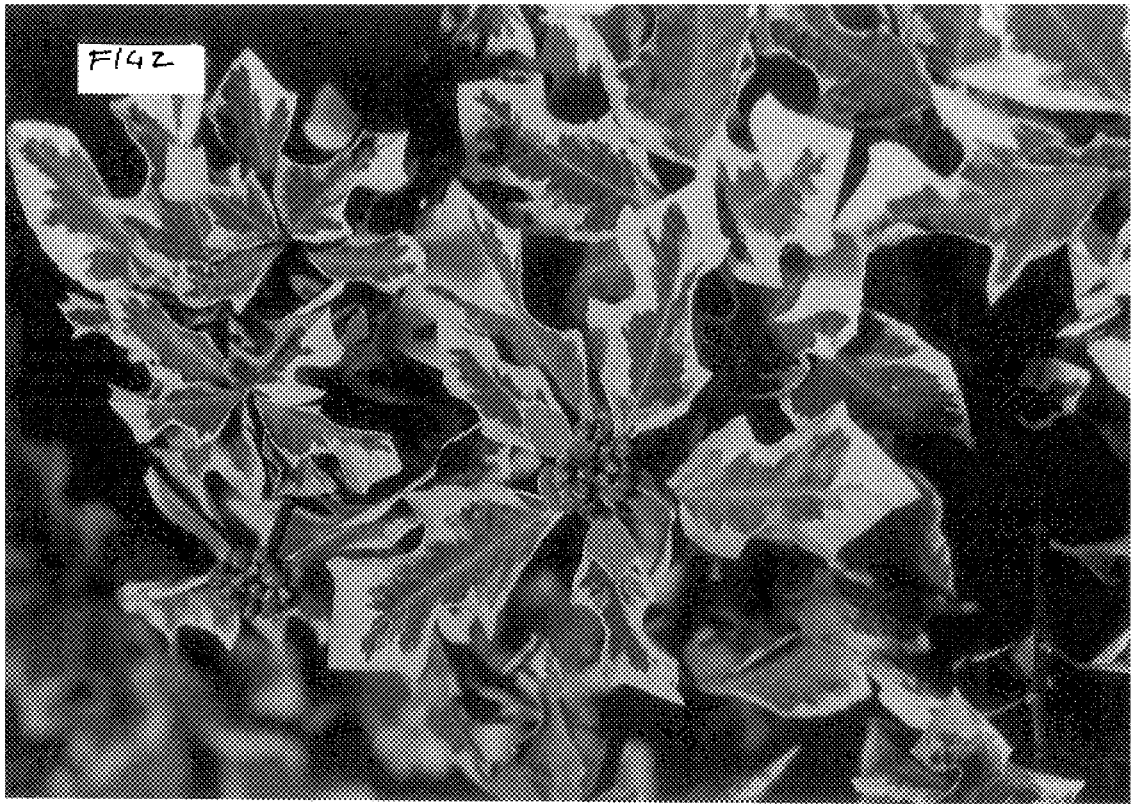

FIG. 1 illustrates the foliage of the new variety, showing the distinctive leaf variegation; and FIG. 2 illustrates the red bracts of the new variety, as well as the distinctive leaf variegation.

DESCRIPTION OF THE NEW VARIETY

*Euphorbia cyathophora* 'YOKOI'S WHITE' has not been observed under all possible environmental, cultural, and light conditions. The following observations and descriptions are of plants grown in containers at Lewisberry, Pa., and Fulshear, Tex. In this description, color references are to The Royal Horticultural Society Colour Chart (1966) and terminology used in the color descriptions herein refers to plate numbers in this color chart. Phenotypic expression may vary with light intensity, cultural, and environmental conditions.

CLASSIFICATION

Botanical: *Euphorbia cyathophora* J. Murray 'YOKOI'S WHITE'.
Parentage: Branch sport of *Euphorbia cyathophora*.
Propagation: Stem cuttings.

PLANT

Size: Between about 50 to 70 cm tall at maturity.
Branching:
*Lateral branches.*—Alternate.
*Typical # branches.*—About 4 to 8 per stem (in a 4" pot).
*Observed # branches.*—Average 6 per stem (in a 4" pot).
*Branch size.*—Between about 4 to 8 cm long.
*Branch diameter.*—Between about 2 to 4 cm.
*Branch coloration.*—Near Green Group 137B to 137C.
Habit: Upright growing herbaceous perennial or annual.
Leaf:
*Shape.*—Most often pandurate, occasionally lanceolate. Apex: Acute. Base: Cuneate.
*Size.*—From about 4 to 6 cm long; about 1.5 to 3.5 cm wide.
*Margin.*—Parted on pandurate leaves; entire on lanceolate leaves.
*Texture substance.*—Upper side: Firm, undulated, nearly hairless. Under side: Leaf surface is firm with midrib slightly pubescent.
*Color.*—The following Color Readings are of 8-month old specimens grown in a heated greenhouse in Fulshear, Tex.
*Young leaves.*—Upper Side: Near Green Group 137C with marginal variegation from near Yellow Group 10B to 10D. Under Side: Near Yellow-Green Group 148C with marginal variegation ranging from near Yellow Group 10C to 10D.
*Mature leaves.*—Upper Side: Leaf center near Green Group 137B, with some smaller patches near 139A; some patches near Green Group 148C approaching marginal variegation; variegation ranging from Yellow Group 8B to 8D. Under side: Leaf center ranging from near Green Group 137B to 137C; marginal variegation ranging from near Yellow Group 11B to 11D, and near White Group 155A near leaf tip.
*Venation.*—Upper Surface: Near Yellow-White Group 158B to 158C. Under Surface: Midrib prominent; near Yellow-White Group 158B to 158C near Yellow-White Group 158B to 158C.
Bracts:
*Arrangement.*—Sometimes fused to foliage; most often separated from foliage.
*Size.*—About to 30 cm long and from 10 to 20 mm wide.
*Color.*—Upper Side: Center area of bract varies in color, ranging from near Orange-Red Group 34A to 35C; bract tip occasionally near White Group 155A. Under Side: No reddish coloration; near Yellow-Green Group 148C; marginal variegation ranging from near Yellow Group 10C to 10D.
Petioles:
*Size.*—Approximately 1 cm long.
*Texture.*—Pubescent.
*Coloration.*—From near Yellow-Green Group 145B to 145C.
*Internodes.*—Between about 1.5 to 2.0 cm.
*Hardiness.*—USDA Zone 9A (25° F. to 20° F.); AHS Heat Zone 1.
*Vigor.*—Average growth rate.
*Pests/diseases.*—No pest or disease problems noted.

INFLORESENCE

Bloom period: June through October (outdoor production area).
Form: Cyathium irregular, clustered at the tops of 2-forked stems and branches.
Size: Between about 2.0 to 2.5 cm across.
Arrangement: Terminal cluster.
Cyathia: From about 2 to 2.5 mm long; or, stalked, to 3 mm long.
Fragrance: None.
Lastingness of individual blooms: About 2 to 3 days per each individual cyathia; entire fluorescence lasts approximately 10 to 14 days.

REPRODUCTIVE ORGANS

Stamens: Monadelphous.
Stigma: *Syncarpous gynoecium.*
Pistils:
*Typical #.*—About 3.
*Observed #.*—3.
Nectaries: 1, occasionally 2, appearing two-lipped.
Capsule: Rounded, 3-lobed, from about 3 to 4.5 mm long.
Seed: Brown; ovoid or rounded; from about 2.5 to 3 mm long.
Pollen:
*Typical amount produced.*—Small amount of pollen produced per anther.
*Observed amount produced.*—Tuft of grains present.
*Color.*—Ranging from near Yellow Group 5A to 5C.
Fruit:
*Type.*—Septicidal capsule.
*Typical amount.*—Between about 4 to 9 inflorescence.
*Observed amount.*—5.
*Length.*—Between about 3 to 5 mm.
*Diameter.*—About 5 mm.
*Color.*—Ranging frm near Yellow-Green Group 145B to 145C.

I claim:

1. A new and distinct *Euphorbia cyathophora* plant of the variety substantially as shown and described.

* * * * *